(12) United States Patent
Poliakoff et al.

(10) Patent No.: US 6,630,606 B2
(45) Date of Patent: Oct. 7, 2003

(54) ACYLATION REACTIONS OF AROMATIC SUBSTRATES

(75) Inventors: Martyn Poliakoff, Beeston (GB); Thomas M. Swan, Bedburn (GB); Thomas Tacke, Paducoh, KY (US); Martin G. Hitzler, Tacherting (DE); Stephen K. Ross, Consett (GB); Stefan Wieland, Offenbach (DE); Fiona Ruth Smail, Beeston (GB)

(73) Assignee: Thomas Swan & Co. Limited, Consett (GB)

( * ) Notice: Subject to any disclaimer, the term of this patent is extended or adjusted under 35 U.S.C. 154(b) by 172 days.

(21) Appl. No.: 09/939,187

(22) Filed: Aug. 24, 2001

(65) Prior Publication Data

US 2002/0062046 A1 May 23, 2002

Related U.S. Application Data

(62) Division of application No. 09/269,894, filed as application No. PCT/GB97/02680 on Sep. 29, 1997, now Pat. No. 6,303,840.

(30) Foreign Application Priority Data

Oct. 4, 1996 (GB) .............................................. 9620745

(51) Int. Cl.$^7$ .......................... C07C 45/46; C07C 49/76
(52) U.S. Cl. ...................... 568/309; 568/319; 568/331; 568/335
(58) Field of Search ................................. 568/309, 319, 568/331, 335

(56) References Cited

FOREIGN PATENT DOCUMENTS

| EP | 0 603 695 A1 | | 6/1994 |
|---|---|---|---|
| EP | 0 603 695 B1 | | 6/1994 |
| JP | 4-247045 | | 2/1991 |
| JP | 6-65112 | | 8/1992 |
| JP | 09059205 | * | 3/1997 |
| WO | WO 97/01014 | | 1/1997 |

OTHER PUBLICATIONS

International Search Report, PCT/GB97/02680. Jan. 22, 1998.

* cited by examiner

Primary Examiner—Johann Richter
Assistant Examiner—Sikarl A. Witherspan
(74) Attorney, Agent, or Firm—Bromberg & Sunstein LLP

(57) ABSTRACT

Method of performing alkylation or acylation reactions of aromatic substrates under supercritical or near-critical reaction conditions. In particular, a method of performing Friedel-Crafts alkylation or acylation reactions is disclosed under those conditions. Friedel-Crafts reactions may be effected using a heterogeneous catalyst in a continuous flow reactor containing a super-critical or near-critical reaction medium. Selectivity of product formation can be achieved by varying one or more of the temperature, pressure, catalyst, flow rates and also by varying the ratios of aromatic substrate to acylating or alkylating agent.

28 Claims, 1 Drawing Sheet

ACYLATION REACTIONS OF AROMATIC SUBSTRATES

CROSS REFERENCE TO RELATED APPLICATIONS

This application is a divisional of U.S. patent Ser. No. 09/269,894 filed Jun. 18,1999 now U.S. Pat. No. 6,303,840, which is based on International Application No. PCTGB97/02680 filed Sep. 29, 1997, which in turn claims priority from British Application No. 9620745.1 filed Oct. 4, 1996.

TECHNICAL FIELD AND BACKGROUND ART

The present invention relates to a novel process for carrying out alkylation and acylation reactions in high yield and high selectivity. More specifically the present invention relates to heterogeneous catalysis of Friedel-Crafts alkylations and acylations in a continuous or semi-batch system under supercritical or near-critical conditions.

BACKGROUND OF THE INVENTION

Although Friedel Crafts alkylations and acylations are industrially important they present various problems for bulk manufacture. The catalysts generally used are Lewis acids such as $AlCl_3$, $FeCl_3$ and $TiCl_4$ or strong protic acids such as hydrofluoric acid or sulfuric acid. All these catalyst present significant health, safety and environmental problems. This is also true of the solvents which are often used e.g. nitrobenzene or chlorinated solvents. In conventional Friedel Craft acylation there is also the problem of disposing of the spent catalyst sludge.

The use of supercritical fluids as a reaction media for carrying out Friedel Crafts alkylation of naphthalene with a zeolite catalyst is known (JP06065112A, JP04247045A2) but the yields are extremely low (less than 5%).

Also, the use of supercritical water as a homogeneous catalyst in a continuous process has been used for mixed alkylation to raise the octane number of gasoline (DE4342501 A1). Although high yielding, this process requires high temperature ($\geq 400°$ C.) and high pressures (25–100 MPa) and such a process would be of little use in selective alkylation for the manufacture of fine organic compounds.

The use of microporous crystalline catalysts such as zeolites, clays and inorganic oxides has also been used to give mixed products in the alkylation of alkenes with isoparaffins (WO 94/03415) for isoparaffin-olefin alkylation.

None of the aforementioned processes would be of benefit on an industrial scale due to either their low yield or low selectivity. The latter two citations are in any case only applicable to gaseous alkylating agents.

The most common industrial use in the fine organic industry of Friedel-Crafts reactions is the alkylation of aromatics, often using an alkene as the alkylating agent, with an acid catalyst.

Accordingly, there is a need for a high yield route to alkylated or acylated aromatic substrates. Desirably, such a route would also allow selective alkylation or acylation of aromatic substrates.

SUMMARY OF THE INVENTION

According to the present invention, there is provided a method of performing an acylation reaction on an aromatic substrate wherein an intimate mixture of the substrate and an alkylating or acylating agent is exposed under supercritical or near-critical conditions to a catalyst which includes a source of acid.

In an embodiment, the catalyst is an acid catalyst which is a Lewis acid, a sulfonic acid, an acidic resin, a zeolite, a modified zeolite, a metal oxide, a clay or a mixed oxide.

It has been found that supercritical fluids not only give an environmental benefit with regard to such processes but also provide a significant rate enhancement compared with conventional solvent systems. Surprisingly, supercritical or near-critical reactions can also be carried out with increased selectivity on a continuous or semi-batch process when using the appropriate catalyst such as those of the present invention. The present invention thus relates to both continuous and semi-batch processes, in contrast with conventional batch-type processes, performed under supercritical or near-critical conditions. Continuous processes have the advantage over such conventional processes that the "downtime" of the apparatus is minimised and that the amounts of waste solvent and unconsumed reactants (which are associated with each complete batch of a conventional batch process) are minimised. Continuous processes in accordance with the invention are thus advantageous over prior art processes.

Using the method of the present invention an acidic resin, a supported Lewis acid catalyst, a sulfonic acid catalyst such as that known as Deloxan.® ASP 1/7 (acylsulfonic acid catalyst on a polysiloxane support ex. Degussa), or one of the other types of catalyst mentioned above results in the formulation of alkylated aromatic substrates in high yield and selectivity. Known Lewis acid catalysts suitable for Friedel-Crafts alkylations and acylations include $AlCl_3$, $FeCl_3$ and $TiCl_4$.

The choice of catalyst may influence whether or not a particular product is formed selectively (where the possibility of more than one product exists) and thus the catalyst may be selected according to the product or products desired from the reaction. It is envisaged that, where appropriate,da combination of two or more suitable catalysts could be used. However, the use of a single catalyst is preferred. Alternatively, or additionally, selectivity may be controlled by independently varying one or more of the temperature, pressure, flow rate (in the case of a continuous process) and concentrations of the reactants.

The present invention also represents the first acylation which has been achieved under supercritical conditions. The acylation reactions according to the present invention are performed using similar conditions as for the alkylation reactions.

Reactions have been carried out in which the supercritical or near-critical fluid (for example, propene) is both the alkylating agent and the solvent. Likewise, the aromatic substrate could function as both the supercritical or near-critical fluid and the reactant. Equally, it is possible for the alkylating reagent and/or the aromatic substrate to be dissolved in a non-reacting supercritical or near-critical fluid such as $CO_2$ or propane. This latter technique is useful for reducing the excess of alkylating agent used and also in cases where the alkylating agent is not a gas at standard temperature and pressure. In such a case the alkylating agent and substrate can be pre-mixed or added separately and dissolved in the non-reacting supercritical or near-critical fluid before passing through the reactor.

The method of the present invention allows a wider range of alkylating agents to be used (such as alkyl halides, alcohols, alkynes, esters, ethers, aldehydes and ketones as well as alkenes and alkanes) than has been used thus far in Friedel-Crafts alkylation. Similarly, for Friedel-Crafts acylation reactions, a wider range of acylating agents may be used than is the case in conventional acylation reactions. Thus carboxylic acids and derivatives thereof e.g. acid anhydrides, esters and acyl halides can be used.

The method of the present invention has the further advantage of being more gentle with the reactants than is the case with conventional reactions so that certain types of substrates which cannot be treated by the conventional acylation reaction may now be acylated. For example, whereas alkyl phenol ethers often suffer ether cleavage and form the substituted alkyl phenol such an undesirable reaction is not observed when the method of the invention is used.

Conventionally the two limiting factors for Friedel-Crafts reactions are the mass transport effect and the reaction rate effect. The use of supercritical fluids in the process of the present invention overcomes the mass transport effect and allows the reaction to be controlled by the reaction kinetic effect. Surprisingly it has been found that kinetic control of the reaction is relatively straightforward and yields greater selectivity in the reaction. Indeed in the alkylation it is possible to select conditions to give mono, di or tri-alkylated products and in the case of mono-alkylated products it is possible by choice of reactor length and catalyst loading to give significant regioselective control of the reaction. We have also found that each increase in pressure of 50 bar gave an increase of approximately 5% in conversion in certain cases. Also surprising was the observation that alkylation of mesitylene with isopropanol could be readily accomplished in 50% yield to give only the mono-product despite literature reports which doubt the ability to form this product by Friedel-Crafts methods (Chem.Ber. 120, 123, 1987).

The reaction will operate in the fluid at temperatures and pressures below the supercritical point of the fluid being used as the solvent, provided that the density of the fluid is sufficient to ensure that the starting materials (reactants) are substantially in a single phase. These conditions are hereafter referred to as being near-critical. Usually, however, the conditions employed will be supercritical.

BRIEF DESCRIPTION OF THE DRAWINGS

The present invention will now be described, by way of example only, with reference to the accompanying drawing (FIG. 1) which is a schematic diagram of a continuous flow reactor according to the present invention and including an additional source of fluid.

DETAILED DESCRIPTION OF SPECIFIC EMBODIMENTS

Figure 1:
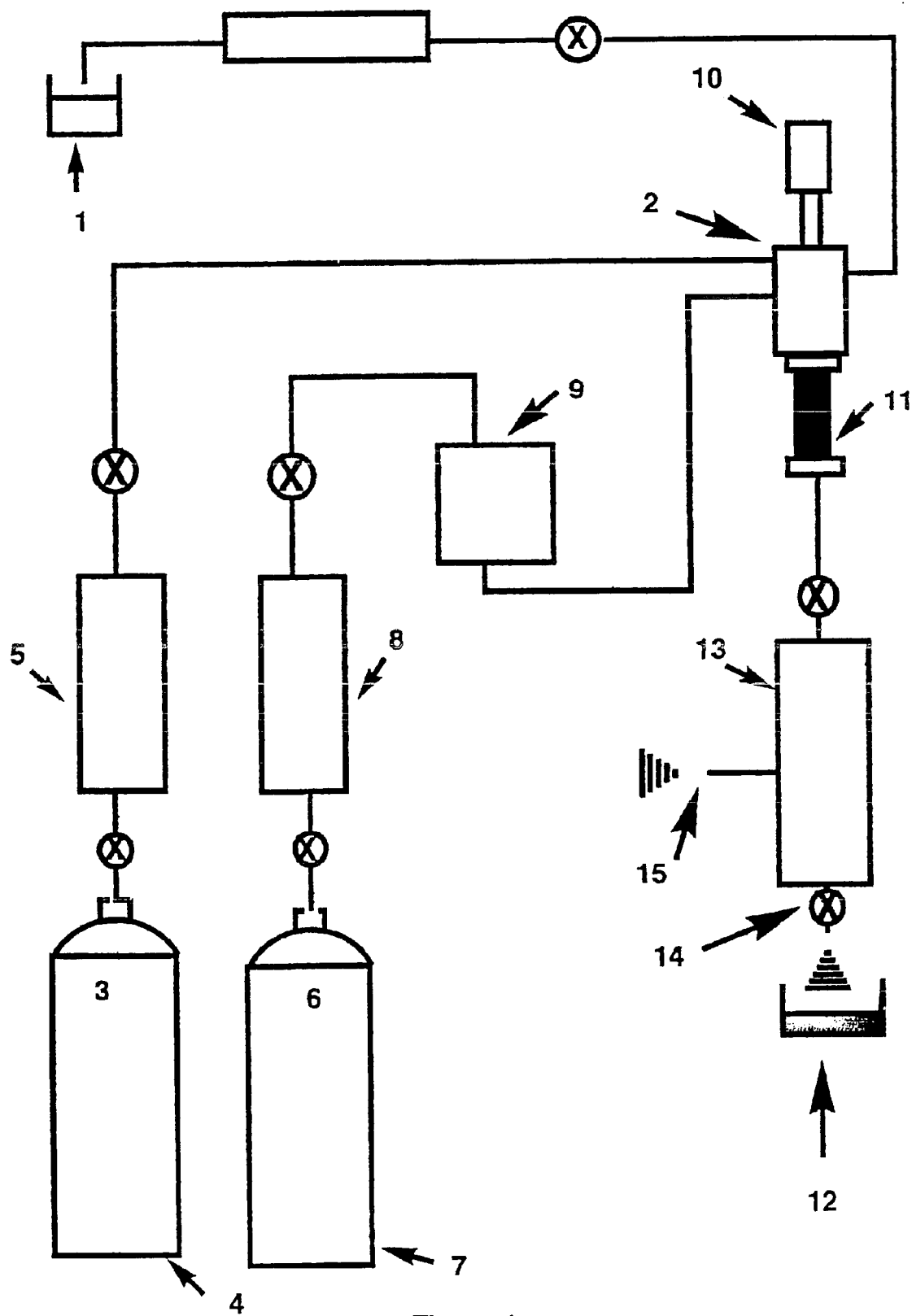

The organic material 1 which may be a mixture of alkylating agent and substrate or substrate alone (or if necessary dissolved in an appropriate solvent) is added via a pump into mixer 2 which may include a stirrer (not shown) where it is mixed with fluid or gas 3 supplied from reservoir 4 via pump 5. The temperature and/or pressure of the mixture is adjusted in the mixer 2 to a temperature and pressure close to or above the supercritical point of fluid 3 as required. Heating means 10 is provided in mixer 2 for this purpose. The mixture is then passed into reactor 11 which contains a catalyst (not shown). After an appropriate residence time in reactor 11, fluid 3 (which contains product 12) is passed into pressure reduction unit 13. The product is removed via a take off tap 14 after passing through pressure reduction unit 13. The flow rate of the reactants through reactor 11 is controlled by a valve (not shown) in pressure reducer 13. The quantity of materials consumed in the reaction and reaction rate are determined by the temperature, the feed rate of organic material 1 into fluid 3 and the flow rate of fluid 3.

Modifications which may be made to the apparatus used in the method of the present invention include (as shown in the drawing) the provision of a source of a further fluid or gas 6 delivered from reservoir 7 via pump 8 and a mixing valve 9 to mixer 2. The additional fluid or gas 6 can be added via a switching valve (not shown) to give the required mole ratio with respect to organic material 1. In such a case, fluid (3) and fluid (6) may be separately in the near-critical or supercritical state, and the resulting fluid mixture may thus be near-critical or supercritical, depending on the conditions.

A further modification to the apparatus of the present invention relates to the addition of a solvent via a pump (not shown) after (i.e. downstream of) the catalyst bed of the reactor. This solvent can be used to dissolve solid products or to remove any hydrogen halide which is formed when using alkyl or acyl halides as the alkylating or acylating agent, respectively.

The following Examples illustrate the invention.

EXAMPLE 1

Alkylation Example

Using an apparatus as shown in the drawing, anisole was added at a rate of 0.2 ml/min into propene with a flow rate of 420 ml/min (at standard temperature and pressure). The temperature was adjusted in the mixer to 200° C. and the pressure was set at 165 bar. The resulting mixture was then heated to 200° C. and passed through the reactor containing 3.45 g of catalyst (Deloxan® ASP 1/7). The reactor outflow was then depressurised and the resulting products analysed.

Conversion of anisole to monoalkyl derivative proceeded in 38% yield.

EXAMPLE 2

Friedel Craft Acylation Example

Using an apparatus as shown in the drawing, anisole and acetic acid (molar ratio of 1:2) were premixed and passed (2 ml/min) into the $CO_2$ stream (flow rate 190 ml/min at standard temperature and pressure). The mixture was then preheated to 200° C. before passing through the reactor containing 2.86 g of catalyst (Deloxan®ASP 1/7). The reactor outflow was then depressurised and the resulting products analysed.

Conversion of anisole to monoacyl derivative proceeded in 8% yield.

Further examples using Deloxan acidic catalysts are given in Schemes 1 to 4 and Tables 1 to 4. It should be appreciated that these results are not fully optimised and represent preliminary findings; it is envisaged that higher yields may be achieved by optimising the conditions.

Scheme 1

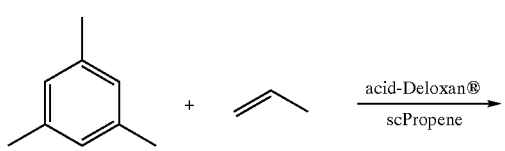

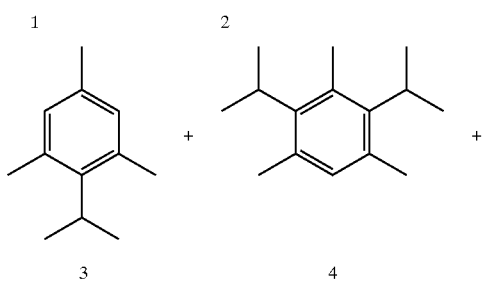

Scheme 2

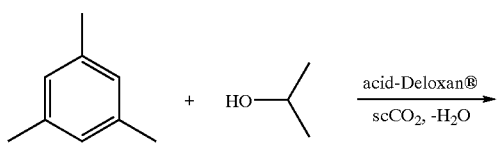

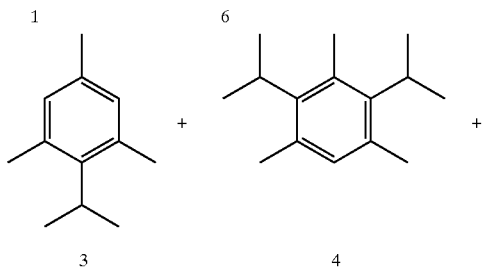

Scheme 3

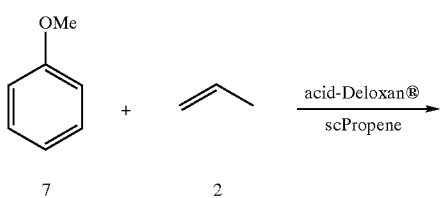

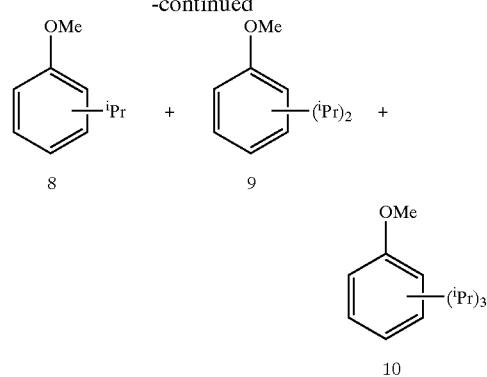

Scheme 4

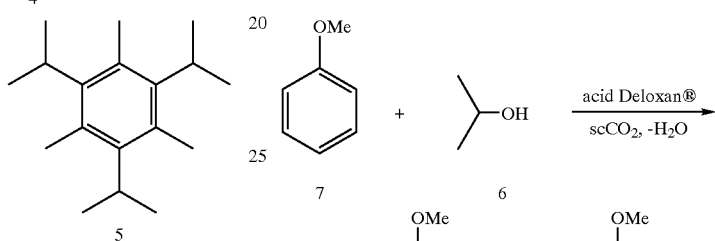

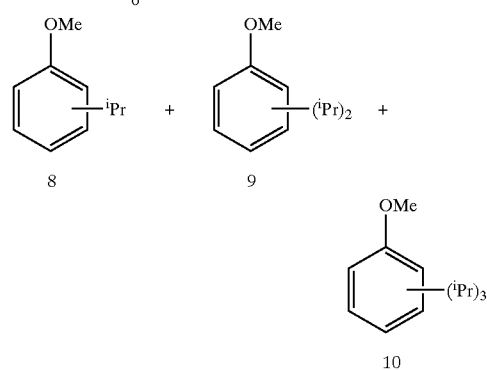

TABLE 1

Alkylation of mesitylene 1 with propene 2 in scPropene (Scheme 1).

| Catalyst T/°C. | Pressure/ bar | Flow Rate of 1 in mL/min | Flow Rate of Propene | Conversion of 1/% | Yield/% 3 | 4 | 5 |
|---|---|---|---|---|---|---|---|
| 160 | 200 | 0.30 | 0.65 | 43 | 25 | 6 | 0 |
| 160 | 200 | 0.30 | 0.43 | 53 | 25 | 10 | 0 |
| 180 | 200 | 0.30 | 0.43 | 68 | 27 | 14 | 2 |

Flow rate of propene in L/min measured at 1 atm and 20° C. as determined by bubble flow meter
Yield as determined by GM-MS.

TABLE 2

Alkylation of mesitylene 1 with isopropanol 6 in scCO$_2$ (Scheme 2).

| Molar ratio 1:6 | Flow Rate of 1 + 6 in mL/min | Flow Rate of CO$_2$ | Catalyst T/°C. | Pressure/ bar | Conversion of 1/% | Yield 3/% |
|---|---|---|---|---|---|---|
| 1.0:3.0 | 0.50 | 0.43 | 200 | 220 | 47 | 40* |
| 2.0:1.0 | 0.70 | 0.65 | 250 | 200 | 42 | 42 |
| 2.0:1.0 | 0.70 | 0.65 | 300 | 200 | 15 | 15 |

TABLE 2-continued

Alkylation of mesitylene 1 with isopropanol 6 in scCO₂ (Scheme 2).

| Molar ratio 1:6 | Flow Rate of 1 + 6 in mL/min | Flow Rate of CO₂ | Catalyst T/° C. | Pressure/ bar | Conversion of 1/% | Yield 3/% |
|---|---|---|---|---|---|---|
| 2.0:1.0 | 0.70 | 0.65 | 250 | 150 | 37 | 37 |
| 5.0:1.0 | 0.56 | 0.65 | 250 | 150 | 50 | 50 |

Flow rate of CO₂ in L/min measured at 1 atm and 20° C. as determined by flow meter
Yield as determined by GC-MS and ¹H NMR.
*Plus 5% of dialkylated product 4.

TABLE 3

Alkylation of anisole 7 with propene 2 in scPropene (Scheme 3).

| Catalyst T/°0 C. | Pressure/ bar | Flow Rate of 7 in mL/min | Flow Rate of Propene | Conversion of 7/% | Yield/% 8 | 9 | 10 |
|---|---|---|---|---|---|---|---|
| 200 | 165 | 0.20 | 0.43 | 64 | 38x | 18y | 5z |

Flow rate of propene in L/min measured at 1 atm and 20° C. as determined by flow meter
Yield as determined by GM-MS.
x Ratio of three isomers 15:13:1.
y Ratio of three isomers 5:2:1.
z Ratio of two isomers 5:2.

TABLE 4

Alkylation of anisole 7 with isopropanol 6 in scCO₂ (Scheme 4).

| Molar ratio 7:6 | Flow Rate of 7 + 6 in mL/min | Flow Rate of CO₂ | Catalyst T/° C. | Pressure/ bar | Conversion of 7/% | Yield 8/% | 9/% |
|---|---|---|---|---|---|---|---|
| 3.0:1.0 | 1.0 | 0.20 | 200 | 220 | 36 | 30x | 6y |

Flow rate of CO₂ in L/min measured at 1 atm and 20° C. as determined by flow meter
Yield as determined by GM-MS.
x Ratio of three isomers 13:12:1.
y Ratio of two isomers 4:1.

What is claimed is:

1. A method for performing an acylation reaction on an aromatic substrate $ArH_n$ to form a product $ArH_{(n-1)}COR$, the method comprising the steps of:
   providing the aromatic substrate,
   intimately mixing the substrate and an acylating agent, and
   exposing an intimate mixture thus formed to a catalyst, wherein exposing occurs in a continuous process under supercritical or near-critical conditions, the catalyst includes a source of acid, wherein reaction conditions of temperature, pressure, flow rate, and reactant concentration and the catalyst are independently controlled and operative to effect product selectivity kinetically favoring a desired product.

2. A method according to claim 1 wherein mixing occurs in the presence of a non-reacting fluid.

3. A method according to claim 1, wherein exposing occurs under supercritical conditions.

4. A method according to claim 2, wherein exposing occurs under supercritical conditions.

5. A method according to claim 1, wherein, in exposing, the catalyst is a heterogeneous catalyst.

6. A method according to claim 3, wherein, in exposing, the catalyst is a heterogeneous catalyst.

7. A method according to claim 4, wherein, in exposing, the catalyst is a heterogeneous catalyst.

8. A method according to claim 1, wherein, in exposing, the catalyst is selected from the group consisting of an acidic resin, a supported Lewis acid catalyst, an organosiloxane-polycondensate, a clay, zeolite, a modified zeolite, a metal oxide, a mixed oxide, and combinations thereof.

9. A method according to claim 2, wherein, in exposing, the catalyst is selected from the group consisting of an acidic resin, a supported Lewis acid catalyst, an organosiloxane-polycondensate, a clay, zeolite, a modified zeolite, a metal oxide, a mixed oxide, and combinations thereof.

10. A method according to claim 3, wherein, in exposing, the catalyst is selected from the group consisting of an acidic resin, a supported Lewis acid catalyst, an organosiloxane-polycondensate, a clay, zeolite, a modified zeolite, a metal oxide, a mixed oxide, and combinations thereof.

11. A method according to claimed 4, wherein, in exposing, the catalyst is selected from the group consisting of an acidic resin, a supported Lewis acid catalyst, an organosiloxane-polycondensate, a clay, zeolite, a modified zeolite, a metal oxide, a mixed oxide,.and combinations thereof.

12. A method according to claim 5, wherein, in exposing, the catalyst is selected from the group consisting of an acidic resin, a supported Lewis acid catalyst, an organosiloxane-polycondensate, a clay, zeolite, a modified zeolite, a metal oxide, a mixed oxide, and combinations thereof.

13. A method according to claim 6, wherein, in exposing, the catalyst is selected from the group consisting of an acidic resin, a supported Lewis acid catalyst, an organosiloxane-polycondensate, a clay, zeolite, a modified zeolite, a metal oxide, a mixed oxide, and combinations thereof.

14. A method according to claim 7, wherein, in exposing, the catalyst is selected from the group consisting of an acidic resin, a supported Lewis acid catalyst, an organosiloxane-polycondensate, a clay, zeolite, a modified zeolite, a metal oxide, a mixed oxide, and combinations thereof.

15. A method according to claim 2, wherein, in mixing, the non-reacting fluid is selected from the group consisting of carbon dioxide and an alkane.

16. A method according to claim 4, wherein, in mixing, the non-reacting fluid is selected from the group consisting of carbon dioxide and an alkane.

17. A method according to claim 9, wherein, in mixing, the non-reacting fluid is selected from the group consisting of carbon dioxide and an alkane.

18. A method according to claim 1, wherein, in exposing, the catalyst includes the aromatic substrate.

19. A method according to claim 1, wherein, in exposing, the catalyst includes the acylating agent.

20. A method according to claim 18, wherein, in exposing, the catalyst includes the acylating agent.

21. A method according to claim 1, wherein, in providing, mixing, and exposing, the substrate, the agent, and the catalyst are included in a homogeneous single phase.

22. A method according to claim 1, wherein the acylation reaction is a Friedel-Crafts acylation reaction.

23. A method for performing an acylation reaction on an aromatic substrate $ArH_n$ to form a product $ArH_{(n-1)}COR$, the method comprising the steps of:
   providing the aromatic substrate,
   intimately mixing the substrate and an acylating agent; wherein the acylating agent is selected from the group consisting of a carboxylic acid derivative, a carboxylic acid, an acid anhydride, an ester, and an acyl halide, and exposing an intimate mixture thus formed to a catalyst,
wherein exposing occurs in a continuous process under supercritical or near-critical conditions, the catalyst includes a source of acid, wherein reaction conditions of temperature, pressure, flow rate, and reactant concentration and the catalyst are independently controlled and operative to effect product selectivity kinetically favoring a desired product.

24. A method according to claim 23, wherein, in mixing, the acylating agent is a carboxylic acid derivative.

25. A method according to claim 23, wherein, in mixing, the acylating agent is an anhydride.

26. A method according to claim 23, wherein, in mixing, the acylating agent is an ester.

27. A method according to claim 23, wherein, in mixing, the acylating agent is anacyl halide.

28. A method according to claim 23, wherein, in mixing, the acylating agent is acetic acid.

* * * * *

UNITED STATES PATENT AND TRADEMARK OFFICE
CERTIFICATE OF CORRECTION

PATENT NO. : 6,630,606 B2
DATED : October 7, 2003
INVENTOR(S) : Thomas Macklyn Swan et al.

It is certified that error appears in the above-identified patent and that said Letters Patent is hereby corrected as shown below:

Column 10,
Line 6, replace "anacyl" with -- an acyl --.

Signed and Sealed this

Second Day of August, 2005

JON W. DUDAS
*Director of the United States Patent and Trademark Office*